(12) United States Patent
Abels

(10) Patent No.: US 6,689,617 B1
(45) Date of Patent: Feb. 10, 2004

(54) AGENT FOR DETECTING MALONDIALDEHYDE, METHOD OF MAKING THE SAME, AND TEST KIT FOR USE THEREOF

(75) Inventor: Robert A. Abels, Long Beach, CA (US)

(73) Assignee: Medi-Tech Holdings, Inc., Los Angeles, CA (US)

( * ) Notice: Subject to any disclaimer, the term of this patent is extended or adjusted under 35 U.S.C. 154(b) by 4 days.

(21) Appl. No.: 10/209,540

(22) Filed: Jul. 30, 2002

(51) Int. Cl.[7] .................. G01N 21/78; G01N 33/493
(52) U.S. Cl. .................. 436/128; 436/166; 436/130; 436/808
(58) Field of Search ................ 436/128, 166, 436/130, 808

(56) References Cited

U.S. PATENT DOCUMENTS

| | | |
|---|---|---|
| 4,753,891 A | 6/1988 | Thompson et al. |
| 5,950,634 A | 9/1999 | Ochi et al. |
| 5,985,665 A | 11/1999 | Crawford et al. |
| 6,165,797 A | 12/2000 | Halstead |

*Primary Examiner*—Jill Warden
*Assistant Examiner*—Monique T. Cole
(74) *Attorney, Agent, or Firm*—Fulbright & Jaworski L.L.P.

(57) ABSTRACT

A reagent for use in detecting the presence of aldehyde particularly in an aqueous solution, urine, or other body fluids comprising a solution sodium metabisulfite, phosphoric acid, basic fuchsin (BA 130) and deionized water. The sodium metabisulfite is present at about 8–12 grams, the phosphoric acid is present at 10 milliliters, the basic fuchsin is present at about 4.8–5.2 grams and the deionized water is present at about 995–1005 milliliters. A test kit including a sealed container having a predetermined amount of the reagent therein, a dispenser for obtaining a predetermined amount of a specimen to be tested and depositing it in the container and a color chart for comparing the color of the combined reagent and specimen after waiting period of between 2–5 minutes. The method of making the reagent by combining the ingredients and mixing the same for at least 10 minutes and then adding 28–32 grams of animal bone charcoal and then stirring the mixture well and allowing it to stand for at least 24 hours and up to 36 hours. Thereafter, the bone charcoal is removed and the decolorized solution is adjusted for a pH between 1.75 and 1.93 by slowly adding phosphoric acid to the mixture and mixing it well during this procedure.

14 Claims, No Drawings

AGENT FOR DETECTING MALONDIALDEHYDE, METHOD OF MAKING THE SAME, AND TEST KIT FOR USE THEREOF

BACKGROUND OF THE INVENTION

1. Field of the Invention

The present invention relates generally to the detection of aldehydes in such media as aqueous solutions, blood, urine and other body fluids and more specifically, to a reagent, the method of making the reagent, and a test kit for using the reagent in the detection of aldehydes and more specifically, malondialdehydes.

2. Description of the Related Art

It is by now common knowledge that stress in mammalian subjects develops directly or indirectly into a display of oxygenated activities that quickly changes the usual reduced state of the body. This hyperoxygenated state—can cause great physical imbalance and actual physical damage that can change to pathological states, which in turn, develop into atherosclerotic plaques. Such plaques can result in the deposition of high lipid levels particularly in a blockage of arteries that can cause a cessation of blood flow to the heart with a resulting heart attack. This is one of but many human disease states that are caused by free radical attacks from the hyperoxygenated state caused by stress.

The oxidative stress state can be measured from the release of aldehydes, particularly as dialdehydes, from the breakdown of long-chain polyunsaturated fatty acids.

We have found that a fuchsin based calorimetric test can measure the released aldehyde in a rapid, easily performed home test kit by using the reagent described below with a small quantity of urine. The resulting color formed is compared to a calibrated test strip to assess the level of stress from a negative value through levels of +1 to +3.

Various test for aldehydes are, of course known. For example, as disclosed at page 395 in "Qualitative Analysis by Spot Tests", Third Edition, authored by F. Feigl and published by Elsevier Publishing Company, Ind., a drop of sample solution which may contain aldehydes in mixed with 2 ml of 72 percent sulfuric acid in a test tube. A small amount of solid chromatropic acid (1,8-dihydrooxynapthianene-3 6 disulfate) is added and the test tube is heated in a 60 degree C. water bath for about ten minutes. A bright violet color appears in the presence of aldehyde sensitivity of the test is reportedly about 3 ppm of aldehyde.

In another aldehyde test, described at pages 339–340 of the Feigl publication, a drop of aqueous (or alcoholic) solution suspected of containing an aldehyde is treated on a spot plate with a drop of sulfurous acid and a drop of fuchsin/sulfiric acid and allowed to stand. A red to blue color appears within about two to thirty minutes, according to the amount of aldehyde present in the test solution being tested. Such test is reportedly sensitive to about one microgram of formaldehyde in a drop of solution being tested. The problem with such a test, and other known aldehyde tests, is that the tests are not quickly and easily performed. The first above-described test, for example, requires heating of a test tube of solution in a constant temperature water bath for ten minutes. As a result of aldehyde tests not being quickly and easily performed, there may be a tendency for the tests for aldehydes not to be performed as frequently as they should or otherwise would be tested.

A further aldehyde test is disclosed in U.S. Pat. No. 6,165,797. As is therein disclosed, urine is tested for presence of malondialdehyde by mixing it with a reagent consisting of about 90–110 parts 20% acetic acid, about 13.5 to 16.5 parts Ingredient A and about 4.5 to 5.5 part Ingredient B, wherein Ingredient A is comprised of sodium metabisulfite, phosphoric acid and the ionized water in the proportions of about 18–22 grams sodium metabisulfite, 9–11 ml of concentrated phosphoric acid, and about 450–550 ml of dionized water, and ingredient B is comprised of basic fuchsin and Ingredient A in the proportion of about 0.45–0.55 grams basic fuchsin to about 90–110 ml Ingredient A. It has been found that the reagent thus formed is much to acidic because of the use of acetic acid and the reaction time when urine is added thereto is extremely quick and results in a color change occurring as a result of the pH of the urine. Thus, false positives occur and it becomes very difficult if not impossible to detect the presence of aldehydes in the urine on a consistent and reliable basis.

For these and other reasons, there is required an improved reagent for reliably detecting the presence of very small amounts of aldehydes in biological fluids so as to detect adverse biological oxidation and therefore decrease medical costs. It is also required that such reagent be packaged in a manner than an individual may easily use it in a home self test.

SUMMARY OF THE INVENTION

An object of the invention is to provide a simple test for determining the presence of aldehyde in a test specimen.

Another object is to provide a test reagent which produces a color change when mixed with a test specimen containing aldehyde.

According to the present invention, a testing solution or reagent for detecting the presence of aldehyde, particularly in an aqueous solution, urine and other body fluids, comprises a solution of phosphoric acid, sodium metabisulfite, basic fuchsin and deionized water. The preferred proportions of the elements for a 1 liter batch are 10 grams sodium metabisulfite, 10 ml concentrated phosphoric acid, 5 grams basic fuchsin and about 1000 ml of water.

Basic fuchsin changes color in an acidic solution, relative to the amount of aldehyde present in the specimen being tested. Basic fuchsin is a purple powder which reacts with aldehydes in the skin, urine or blood plasma. With low or no aldehydes present, you get no color development. With moderate or high levels of aldehydes you get color gradations roughly dependent on the level of aldehydes present. The amino group of the fuchsin couples with the aldehyde to produce the pink to purple color approximately dependent on the amount of aldehyde present in the biological fluids such as blood or urine. The color developed depends on the pH, which is controlled by the amount of acid present.

Sodium metabisulfite is a reducer to stop the interference of oxygen from air. Metabisulfite ties up free oxygen so that only the aldehydes react with the fuchsin group. Establishing a nitrogen blanket over the reagent mixture gives greater shelf life to the reagent by stopping any oxygen reaction with the reagent. The phosphoric acid stabilizes the pH.

Aldehydes are released from the breakdown of long chain polyunsaturated fatty acids by free radical attacks.

High levels of aldehydes are found in a variety of diseases and abnormal metabolism states such as coronary artery disease, diabetes, and Parkinson disease.

A method for testing for aldehydes in an aqueous solution, urine, blood and other body fluids comprises mixing a test specimen such as urine suspected of containing traces of aldehydes into the testing reagent described above, and observing for color formation after at least 2 minutes, preferably 2–5 minutes. The preferred proportions are about 0.9 to 1.1 ml of the test specimen to about 0.1–0.2 ml of the testing reagent. If the mixture does not become colored within such time, the test specimen contains less than about 2 ppm of aldehyde. If, however, the mixture becomes colored, for example, pinkish-purple, within the time specified, or sooner, aldehyde presence of greater than 2 ppm in the test specimen is inferred, the more intense the color, the greater the concentration of aldehyde.

Preferably, the testing reagent is contained in a sealed ampule or vial. Test specimen is introduced to the reagent in a snap-type ampule. A simple, efficient, reliable and rapid test for the presence of aldehyde in aqueous solution is thereby provided. Typically, the ampule along with an appropriate dispenser such as a syringe or pipette and a container for collecting the specimen are housed in a package bearing a color chart. This provides an easy, reliable way for an individual to test for the presence of aldehydes in his or her urine.

DESCRIPTION OF THE PREFERRED EMBODIMENT

According to the present invention, a method of making the reagent is as follows: First, dissolve about 8–12 grams of sodium metabisulfite in about 995–1005 ml of dionized water, then add 10 ml of phosphoric acid and about 4.8 to 5.2 grams of basic fuchsin. The basic fuchsin is identified as BA 130 from Spectrum Chemical. The mixture should be mixed for at least 10 minutes and then add about 28–32 grams of animal bone charcoal. The mixture should then be well mixed and should remain standing for at least 24 hours and up to 36 hours. Thereafter, the bone charcoal is removed by centrifuging and filtering the mixture. The animal bone charcoal removes the color from the mixture thus, providing a decolorized solution. This decolorized solution is then adjusted for a pH between 1.75 and 1.93 by slowly adding phosphoric acid to the mixture and mixing it well during this procedure.

According to the present invention, a preferred method of making the reagent is as follows: First, dissolve 10 grams of sodium metabisulfite in 1000 ml of deionized water. Then add 10 ml of phosphoric acid and 5 grams of basic fuchsin (BA 130). The mixture should be mixed for at least 10 minutes. Then add 30 grams of animal bone charcoal. The mixture should then be well mixed and should remain standing for at least 24 hours. At this time, the bone charcoal is removed by centrifuging and filtering the mixture.

At this time, the decolorized solution should be adjusted for pH. The pH should be gradually adjusted by adding phosphoric acid until it reaches a level of 1.88. It is important that the phosphoric acid be added slowly and mixed well during this procedure.

The testing solution described above is preferably stored in individual, sealed test-size ampules or vials of conventional medical solution type. When packaged in such a manner and stored in a cool, dry place, the sealed bottle or vials have an expected shelf storage life of at least 12 months. Assurance of accurate testing solution may be achieved as descried below, by positive aldehyde test procedures.

A test for the presence of aldehyde in an aqueous solution is then made by mixing about 0.9 ml of test solution (containing traces of aldehyde) into about 0.1 ml of testing solution formulated as above. In a preferred embodiment of the test kit, the ampule is a 1 ml volume ampule containing 0.1 ml of the reagent sealed therein. The top of the ampule is broken off about a score line and discarded. The dispenser is used to fill the ampule with about 0.9 ml of urine. If the mixture of the test sample and testing solution remains colorless after a waiting period of about 2–5 minutes, the test is negative and the test sample therefore contains less than about 2 ppm aldehyde. Any color change of the mixture indicates presence of aldehyde in the test solution in a concentration greater than about 2 ppm.

A positive aldehyde test is preferably by quality control techniques made before testing the test samples to assure that the testing solution is properly formulated or that, for example, the reagent bottles have not been replaced with other bottles containing non-testing solutions.

The positive aldehyde test is preferably performed by injecting 1 ml of available "Positive Aldehyde Test Solution (Standard)" into a bottle containing about 0.2–0.6 ml of test solution. In approximately 2–5 minutes, the solution in the bottle should develop a pinkish-purple color provided the bottle contains properly formulated aldehyde testing solution. Otherwise, the bottle of "testing solution" from which the test bottle was selected should be discarded. The above-described positive test for aldehyde is sensitive to 10 ppm or more of aldehyde. For a 5 ppm, a positive test for aldehyde, 0.5 ml of deionized water is used. A colorless intense than that of the 10 ppm aldehyde test is obtained for the 5 ppm aldehyde test.

There has thus been disclosed a reagent for use in detecting the presence of aldehydes in biological fluids, a method of making the reagent and a test kit including the reagent for use by an individual.

What is claimed is:

1. A test kit for use by an individual for detecting the presence of malondialdehyde in urine comprising:
    a sealed container having a predetermined amount of a reagent therein;
    said reagent, for approximately a liter batch comprising about 8–12 grams of sodium metabisulfite, about 995 to 1005 milliliters of deionized water, 10 milliliters of phosphoric acid, about 4.8 to 5.2 grams of basic fuchsin (BA130) and having a pH of between 1.75 and 1.93;
    a receptacle for collecting a specimen of urine;
    a dispenser for removing a predetermined amount of said urine from said receptacle and depositing it in said container after the seal on said container is broken; and
    a color chart for comparing the color of the combined reagent and urine after a waiting period of between 2–5 minutes, the color of the combined reagent and urine indicating the absence or presence of aldehyde in the urine.

2. A test kit as defined in claim 1 wherein said sealed container has a 1 ml volume capacity and said predetermined amount of reagent contained therein is 0.1 ml.

3. A test kit as defined in claim 1 wherein said sodium metabisulfite is present in the amount of 10 grams.

4. A test kit as defined in claim 1 wherein said basic fuchsin (BA 130) is present in the amount of 5.0 grams.

5. A test kit as defined in claim 1 wherein the pH of said reagent is 1.88.

6. A reagent for use in detecting the presence of aldehyde in urine comprising about 8–12 grams of sodium metabisulfite, about 999–1005 milliliters of deionized water, 10 milliliters of phosphoric acid, about 4.8–5.2 grams of basic fuchsin (BA 130) and having a pH of between 1.75 and 1.93.

7. A reagent as defined in claim 6 wherein the sodium metabisulfite is present at 10 grams.

8. The reagent as defined in claim 7 wherein the basic fuchsin (BA 130) is present at 5 grams.

9. The reagent as defined in claim 8 wherein the pH is 1.88.

10. The method of making a reagent for use in detecting the presence of aldehyde in urine in an approximately 1 liter batch comprising the steps of:

dissolving about 8–12 grams of sodium metabisulfite in about 995–1005 ml of deionized water, adding 10 milliliters of phosphoric acid, adding about 4.8–5.2 grams of basic fuchsin (BA 130), mixing the foregoing ingredients for at least 10 minutes, add about 28–32 grams of animal bone charcoal and mixing until the bone charcoal is well distributed, allowing the resulting mixture to stand for between 24 hours and 36 hours, removing the bone charcoal, and adjusting the pH of the mixture by adding phosphoric acid until it reaches a pH of between 1.75 and 1.93.

11. The method as defined in claim 10 wherein said sodium metabisulfite is present at 10 grams.

12. The method as defined in claim 10 wherein said basic fuchsin (BA130) is present at 5 grams.

13. The method as defined in claim 10 wherein said animal bone charcoal is present at 30 grams.

14. The method as defined in claim 1 wherein said pH level is adjusted to 1.88 by slowly adding phosphoric acid and stirring well.

* * * * *